United States Patent

Normen

(10) Patent No.: US 6,704,666 B2
(45) Date of Patent: Mar. 9, 2004

(54) DETERMINING PROPERTIES OF A FLOW TUBE AND OF A FLUID FLOWING THROUGH A FLOW TUBE OF A CORIOLIS FLOWMETER

(75) Inventor: David F. Normen, Louisville, CO (US)

(73) Assignee: Micro Motion, Inc., Boulder, CO (US)

(*) Notice: Subject to any disclaimer, the term of this patent is extended or adjusted under 35 U.S.C. 154(b) by 191 days.

(21) Appl. No.: 09/941,332

(22) Filed: Aug. 29, 2001

(65) Prior Publication Data

US 2003/0055580 A1 Mar. 20, 2003

(51) Int. Cl.$^7$ .............................. G01F 1/20
(52) U.S. Cl. ........................ 702/45; 73/861.355
(58) Field of Search ................ 73/861.355–861.357; 702/45–49, 100

(56) References Cited

U.S. PATENT DOCUMENTS

| | | | | |
|---|---|---|---|---|
| 6,092,409 A | * | 7/2000 | Patten et al. .............. | 73/1.34 |
| 6,249,752 B1 | * | 6/2001 | Cunningham et al. ...... | 702/100 |
| 6,272,438 B1 | | 8/2001 | Cunningham et al. | |
| 6,347,293 B1 | * | 2/2002 | Cunningham et al. ...... | 702/189 |
| 6,466,880 B2 | * | 10/2002 | Cunningham et al. ........ | 702/50 |

OTHER PUBLICATIONS

Stack, C. P., Garnett, R. B. And Pawlas, G. E.; AIAA Paper No. 93–1552, "A Finite Element For the Vibration Analysis of a Fluid–Conveying Timoshenko Beam," American Institute of Aeronautics and Astronautics, Inc.; Apr. 19, 1993; pp. 2120–2129.

\* cited by examiner

*Primary Examiner*—Marc S. Hoff
*Assistant Examiner*—Edward Raymond
(74) *Attorney, Agent, or Firm*—Duft Setter Ollila & Bornsen LLC

(57) ABSTRACT

A process is disclosed for determining properties of a flow tube and of a fluid flowing through the flow tube. One example of such a property is the density of the fluid flowing through the flow tube. To determine the properties, the process determines a measured mode shape based on pickoff signals received from a plurality of pickoffs. The process selects values for flow tube and fluid parameters. The process determines an estimated mode shape based on the values for the flow tube and fluid parameters. The process compares the measured mode shape and the estimated mode shape to determine an error for the values for the flow tube and fluid parameters. If the error for the values is within an error range, then the process determines the properties of the flow tube and of the fluid based on the estimated values. If the error for the values is not within the error range, then the process selects new values for the flow tube and fluid parameters.

20 Claims, 11 Drawing Sheets

US 6,704,666 B2

DETERMINING PROPERTIES OF A FLOW TUBE AND OF A FLUID FLOWING THROUGH A FLOW TUBE OF A CORIOLIS FLOWMETER

FIELD OF THE INVENTION

The invention relates to Coriolis flowmeters, and in particular, to methods and systems for measuring properties of a flow tube and of a material flowing through the flow tube.

STATEMENT OF THE PROBLEM

Coriolis flowmeters measure mass flow and other information for fluids flowing through a flow tube in the flowmeter. Coriolis flowmeters are comprised of a Coriolis sensor and associated meter electronics. Exemplary Coriolis flowmeters are disclosed in U.S. Pat. No. 4,109,524 of Aug. 29, 1978, U.S. Pat. No. 4,491,025 of Jan. 1, 1985, and Re. 31,450 of Feb. 11, 1982, all to J. E. Smith et al. These flowmeters have one or more flow tubes of a straight or a curved configuration. Each flow tube configuration in a Coriolis flowmeter has a set of natural modes of vibration, which may be of a simple bending, twisting, torsional, or coupled type. Each flow tube is driven to oscillate at a resonance in one of these natural modes of vibration. Fluid flows into the flowmeter from a connected pipeline on the inlet side of the flowmeter, is directed through the flow tube or flow tubes, and exits the flowmeter through the outlet side of the flowmeter. The natural vibration modes of the vibrating, fluid-filled system are defined in part by the combined mass of the flow tubes and the fluid flowing through the flow tubes.

When there is no flow through the flowmeter, all points along the flow tube oscillate, due to an applied driver force, with substantially identical phase or small initial fixed phase offset which can be corrected. As fluid begins to flow, Coriolis forces cause points along the flow tube to have a different phase. The phase on the inlet side of the flow tube commonly lags the driver, while the phase on the outlet side of the flow tube leads the driver. Pickoffs are affixed to the flow tube to measure the motion of the flow tube and to produce sinusoidal pickoff signals representative of the motion of the flow tube. The meter electronics processes pickoff signals to determine the phase difference between the pickoff signals. The phase difference between two pickoff signals is proportional to the mass flow rate of fluid through the flow tube.

An important component of Coriolis flowmeters, and of vibrating tube densitometers, is the drive or excitation system. The drive system operates to apply a periodic physical force to the flow tube which causes the flow tube to oscillate. The drive system includes a driver mechanism mounted to the flow tube of the flowmeter and a drive circuit for generating a drive signal to operate the driver mechanism. The driver mechanism typically contains one of many well known arrangements, such as a magnet mounted to one flow tube and a wire coil mounted to the another flow tube or brace bar in an opposing relationship to the magnet.

A drive circuit continuously applies a periodic drive voltage to the driver mechanism. The drive voltage is typically sinusoidally or square shaped. In a typical magnetic-coil drive mechanism, the periodic drive voltage causes the coil to produce a continuous alternating magnetic field. The alternating magnetic field of the coil and the constant magnetic field produced by the magnet force the flow tube to vibrate in a sinusoidal pattern. Those skilled in the art will recognize that any device capable of converting an electrical signal to mechanical force is suitable for application as a driver. (See, U.S. Pat. No. 4,777,833 issued to Carpenter and assigned on its face to Micro Motion, Inc.) Also, one need not use a sinusoidal signal but rather any periodic signal may be appropriate as the driver signal (See, U.S. Pat. No. 5,009,109 issued to Kalotay et. al. and assigned on its face to Micro Motion, Inc.).

For a dual tube flowmeter, a typical mode in which Coriolis flowmeters are typically driven to vibrate is a first out-of-phase bending mode. The first out-of-phase bending mode is the fundamental bending mode at which the two flow tubes of a dual tube Coriolis flowmeter vibrate in opposition to one another. However, this is not the only mode of vibration present in the vibrating structure of a Coriolis flowmeter driven in the first out-of-phase bending mode. Higher modes of vibration may also be excited in the flow tubes. For example, a first out-of-phase twist mode may be excited as a result of a fluid flowing through the vibrating flow tube and the Coriolis forces caused by the flowing fluid. Other higher modes of vibration that may be excited include in-phase and lateral modes of vibration. There may be hundreds of vibration modes actually excited in a Coriolis flowmeter that is driven to oscillate in the first out-of-phase bending mode. Even within a relatively narrow range of frequencies near the first out-of-phase bending mode, there are at least several additional modes of vibration that are excited by the vibration of the flow tube by the drive system. In addition to multiple modes being excited by the driver, additional undesired modes of vibration can also be excited due to vibrations external to the flowmeter. For example, a pump located elsewhere in a process line might generate a vibration along a pipeline that excites a mode of vibration in a Coriolis flowmeter.

As discussed above, the driver vibrates the flow tube at a resonant frequency. As the density of the fluid inside the flow tube changes, the resonant frequency changes. The change in resonant frequency squared is inversely proportional to the change in density, as described in the following equation:

$$\Delta f^2 = \frac{K}{\Delta \rho}$$

where f represents the resonant frequency, K represents a proportionality constant, and $\rho$ represents density. The period ($\tau$) of the resonant frequency can also be used, as described in the following equation:

$$\Delta \rho = K \Delta \tau^2$$

where $\tau$ represents the period of the resonant frequency. Users of Coriolis flowmeters may want to measure the absolute density rather than the relative change in fluid density. A calibration of the Coriolis flowmeter may be required to determine a proportionality constant K and a reference fluid density. Calibration of the Coriolis flowmeter is accomplished by measuring the frequency/period of resonance with two known fluids. The absolute fluid density can be calculated using the following equation:

$$\rho_{measured} = \left[ \frac{\rho_2 - \rho_1}{\tau_2^2 - \tau_1^2} \right] (\tau_{measured}^2 C(T) - \tau_1^2) + \rho_1$$

where $\tau_1$ and $\tau_2$ represent the tube period using two known fluids and $\rho_1$ and $\rho_2$ represent the densities of the two known fluids. C(T) is a temperature compensation for changes in the material of the Coriolis flowmeter due to temperature.

Unfortunately, the temperature of the fluid is often different than the ambient temperature around the flowmeter. The flow tube of the Coriolis flowmeter may grow or shrink due to thermal expansion. For a curved tube flowmeter, the thermal expansion may not be a problem because the flow tube is free to expand or shrink. For a straight tube flowmeter, the thermal expansion of the flow tube may be a problem because the flow tube is constrained from expansion along its axis by a case, a brace bar, or other means. The thermal expansion can result in a change in the resonant frequency due to temperature even though the fluid density may be unchanged. The meter electronics can compensate for the thermal expansion using a temperature correction, but the meter electronics have not been effectively adapted to handle thermal expansion by a more reliable means. This temperature correction is an indirect estimate of the tension/compression because it assumes a coefficient of thermal expansion.

Straight tube flowmeters are generally more sensitive to changes in boundary conditions than are curved tube flowmeters. Boundary conditions are the forces and moments that restrain the motion of a vibrating flow tube. Conversely, dual curved tube flowmeters are naturally counterbalanced, so the forces and moments exerted by the two flow tubes sum to zero. Some straight tube flowmeters utilize counterbalance systems to passively or actively oppose the boundary forces and moments exerted by a single flow tube. Passive counterbalance systems unfortunately only work well over a limited range of fluid densities. Active counterbalance systems add additional complexity to the flowmeter. Thus, problems caused by temperature changes and boundary condition changes are especially evident in straight tube flowmeters.

Properties of the flow tube and of the fluid flowing through the flow tube is useful information to obtain from a flowmeter. Properties of the flow tube and of the fluid flowing through the flow tube include the fluid density, the tension/compression in the flow tube, and flow tube's material density, the pressure in the flow tube, and other properties. Unfortunately, accurate measurement of the properties of the flow tube and of the fluid flowing through the flow tube are currently difficult to obtain without compensating for conditions such as temperature changes and boundary condition changes.

STATEMENT OF THE SOLUTION

The above and other problems are solved and an advance in the art is made by a system and method for determining properties of the flow tube and of the fluid flowing through the flow tube. The present invention determines the properties of the flow tube and of the fluid flowing through the flow tube without having to directly compensate for temperature changes and boundary condition changes in a straight tube flowmeter.

In accordance with this invention, meter electronics execute instructions that provide a process for determining properties of a flow tube and of a fluid flowing through the flow tube. The process begins when the meter electronics receives pickoff signals from a plurality of pickoffs. The meter electronics determines a measured mode shape of the flow tube based on the pickoff signals. The meter electronics then selects values for flow tube and fluid parameters. The flow tube and fluid parameters are any parameters that represent physical properties of a flow tube or of a fluid flowing through the flow tube. The meter electronics then determines an estimated mode shape of the flow tube based on the values for the flow tube and fluid parameters. The meter electronics compares the estimated mode shape to the measured mode shape to determine an error for the values for the flow tube and fluid parameters. The meter electronics determines if the error for the values for the flow tube and fluid parameters is within an error range. If the error for the values is within the error range, then the meter electronics determines the properties of the flow tube and of the fluid flowing through the flow tube based on at least one of the values for the flow tube and fluid parameters.

In some examples, if the error for the values is not within the error range, then the meter electronics selects new values for the flow tube and fluid parameters. The meter electronics then repeats the above process using the new values.

In some examples, one of the properties of the flow tube and of the fluid being determined is the density of the fluid. In order to determine the density, the meter electronics may have to determine one or more density calibration factors. The determination of the density calibration factors may include flowing a first fluid of a known density through the flow tube. The meter electronics receives pickoff signals indicating motion of the flow tube as the first fluid flows through the flow tube. The determination further includes flowing a second fluid of a known density through the flow tube. The meter electronics receives pickoff signals indicating motion of the flow tube as the second fluid flows through the flow tube. The meter electronics determines the density calibration factors from the pickoff signals received responsive to the first and the second fluids flowing through the flow tube.

One aspect of the invention includes a method for determining properties of a flow tube and of a fluid flowing through said flow tube in response to receiving pickoff signals from a plurality of pickoffs associated with said flow tube, said pickoff signals indicating vibrations of said flow tube vibrated by a driver associated with said flow tube, said method comprising the steps of:

a) receiving said pickoff signals from said plurality of pickoffs;
b) determining a measured mode shape of said flow tube based on said pickoff signals;
c) selecting values for flow tube and fluid parameters;
d) determining an estimated mode shape of said flow tube based on said flow tube and fluid parameters;
e) comparing said estimated mode shape to said measured mode shape to determine an error for said values for said flow tube and fluid parameters; and
f) if said error for said values for said flow tube and fluid parameters is within an error range, then:
   determining said properties of said flow tubes and of said fluid flowing through said flow tube based on said values for said flow tube and fluid parameters.

Another aspect of the invention includes a method further comprising:

(g) if said error for said values for said flow tube and fluid parameters is not within said error range, then:
   selecting new values for said flow tube and fluid parameters; and
   repeating steps (d)–(g).

Another aspect of the invention includes a method wherein the step of determining said properties of said flow tube and of said fluid flowing through said flow tube comprises:

determining a density of said fluid flowing through said flow tube based on said values for said flow tube and fluid parameters.

Another aspect of the invention includes a method further comprising the steps of:
flowing a first fluid of a known density through said flow tube and receiving said pickoff signals indicating motion of said flow tube as said first fluid flows through said flow tube to generate first factors;
flowing a second fluid of a known density through said flow tube and receiving said pickoff signals indicating motion of said flow tube as said second fluid flows through said flow tube to generate second factors; and
determining density calibration factors based on said first and second factors;
wherein said step of determining said density of said fluid flowing through said flow tube further comprises determining said density of said fluid flowing through said flow tube based on said values for said flow tube and fluid parameters and said density calibration factors.

Another aspect of the invention includes a method wherein a first one of said density calibration factors comprises a ratio of area per unit length of said fluid to a flexural rigidity of said flow tube.

Another aspect of the invention includes a method wherein a second one of said density calibration factors comprises a ratio of mass per unit length of said flow tube to said flexural rigidity of said flow tube.

Another aspect of the invention includes a method wherein:
a first one of said values for said flow tube and fluid parameters comprises a ratio of mass per unit length of said fluid and said flow tube to said flexural rigidity of said flow tube; and
said step of determining said density of said fluid flowing through said flow tube comprises:
subtracting said second one of said density calibration factors from said first one of said values for said flow tube and fluid parameters to yield a first result; and
multiplying said first result by an inverse of said first one of said density calibration factors to determine said density of said fluid flowing through said flow tube.

Another aspect of the invention includes a method wherein said plurality of pickoffs comprises at least four boundary condition pickoffs affixed to said flow tube and configured to generate said pickoff signals.

Another aspect of the invention includes a method wherein said plurality of pickoffs further comprises at least one reference pickoff affixed to said flow tube and configured to generate a reference signal.

Another aspect of the invention includes a method wherein said step of determining said new values for said flow tube and fluid parameters comprises comparing said flow tube and fluid parameters from at least two modes of vibration of said flow tube to determine said new values.

Another aspect of the invention includes meter electronics configured to determine properties of a flow tube and of a fluid flowing through said flow tube in response to receiving pickoff signals from a plurality of pickoffs associated with said flow tube, said signal indicating vibrations of said flow tube being vibrated by a driver associated with said flow tube, said meter electronics comprising: a processing unit configured to read instructions from a storage media; and said instructions configured to direct said processing unit to:
a) receive said pickoff signals from said plurality of pickoffs;
b) determine a measured mode shape of said flow tube based on said pickoff signals;
c) select values for flow tube and fluid parameters;
d) determine an estimated mode shape of said flow tube based on said flow tube and fluid parameters;
e) compare said estimated mode shape to said measured mode shape to determine an error for said values for said flow tube and fluid parameters; and
f) if said error for said values for said flow tube and fluid parameters is within an error range, then:
determine said properties of said flow tube and of said fluid flowing through said flow tube based on said values for said flow tube and fluid parameters.

Another aspect of the invention includes meter electronics wherein said instructions are further configured to direct said processing unit to:
(g) select new values for said flow tube and fluid parameters; and
repeat steps (d)–(g) if said error for said values for said flow tube and fluid parameters is not within said error range.

Another aspect of the invention includes meter electronics wherein said instructions are further configured to direct said processing unit to:
determine a density of said fluid flowing through said flow tube based on said values for said flow tube and fluid parameters.

Another aspect of the invention includes meter electronics wherein said instructions are further configured to direct said processing unit to:
generate first factors in response to receiving said pickoff signals indicating motion of said flow tube as a first fluid of a known density flows through said flow tube;
generate second factors in response to receiving said pickoff signals indicating motion of said flow tube as a second fluid of a known density flows through said flow tube;
determine density calibration factors based on said first and second factors; and
determine said density of said fluid flowing through said flow tube based further on said density calibration factors.

Another aspect of the invention includes meter electronics wherein a first one of said density calibration factors comprises a ratio of area per unit length of said fluid to a flexural rigidity of said flow tube.

Another aspect of the invention includes meter electronics wherein a second one of said density calibration factors comprises a ratio of mass per unit length of said flow tube to said flexural rigidity of said flow tube.

Another aspect of the invention includes meter electronics wherein:
a first one of said values for said flow tube and fluid parameters comprises a ratio of mass per unit length of said fluid and said flow tube to said flexural rigidity of said flow tube; and
wherein said instructions that are configured to direct said processing unit to determine said density of said fluid are further configured to direct said processing unit to:
subtract said second one of said density calibration factors from said first one of said values for said flow tube and fluid parameters to yield a first result; and
multiply said first result by an inverse of said first one of said density calibration factors to determine said density of said fluid flowing through said flow tube.

Another aspect of the invention includes meter electronics wherein said plurality of pickoffs comprises at least four boundary condition pickoffs affixed to said flow tube and configured to generate said pickoff signals.

Another aspect of the invention includes meter electronics wherein said plurality of pickoffs further comprises at least one reference pickoff affixed to said flow tube and configured to generate a reference signal.

Another aspect of the invention includes meter electronics wherein said instructions that are configured to direct said processing unit to determine said new values for said flow tube and fluid parameters are further configured to direct said processing unit to compare said flow tube and fluid parameters from at least two modes of vibration of said flow tube to determine said new values.

DESCRIPTION OF THE DRAWINGS

The above and other features of the invention can be understood from reading the detailed description and the following drawings.

DETAILED DESCRIPTION

Figure 1:
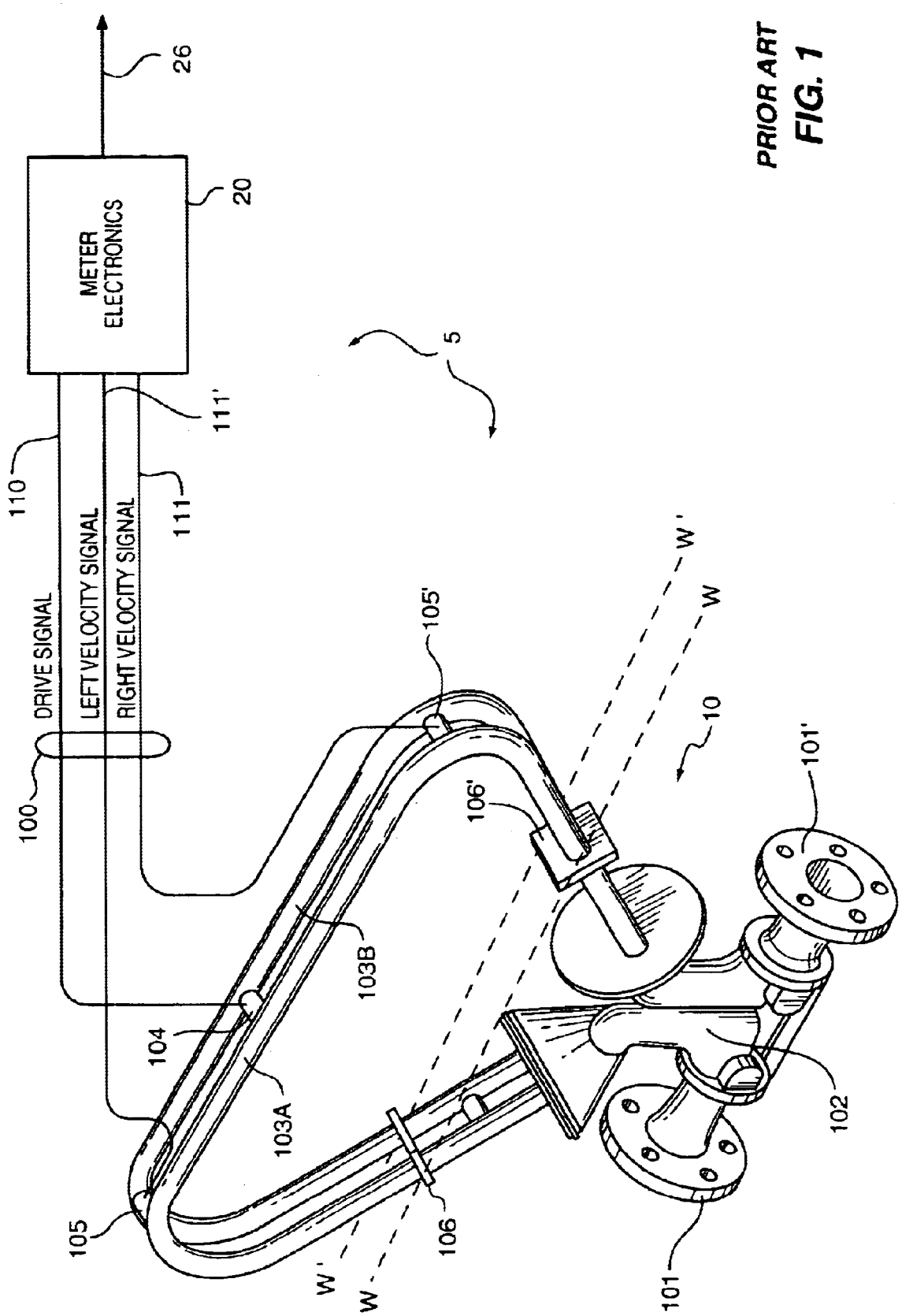
FIG. 1 illustrating a dual flow tube Coriolis flowmeter incorporating a system for determining properties of the flow tube and of a fluid flowing through the flow tube.
Figure 2:
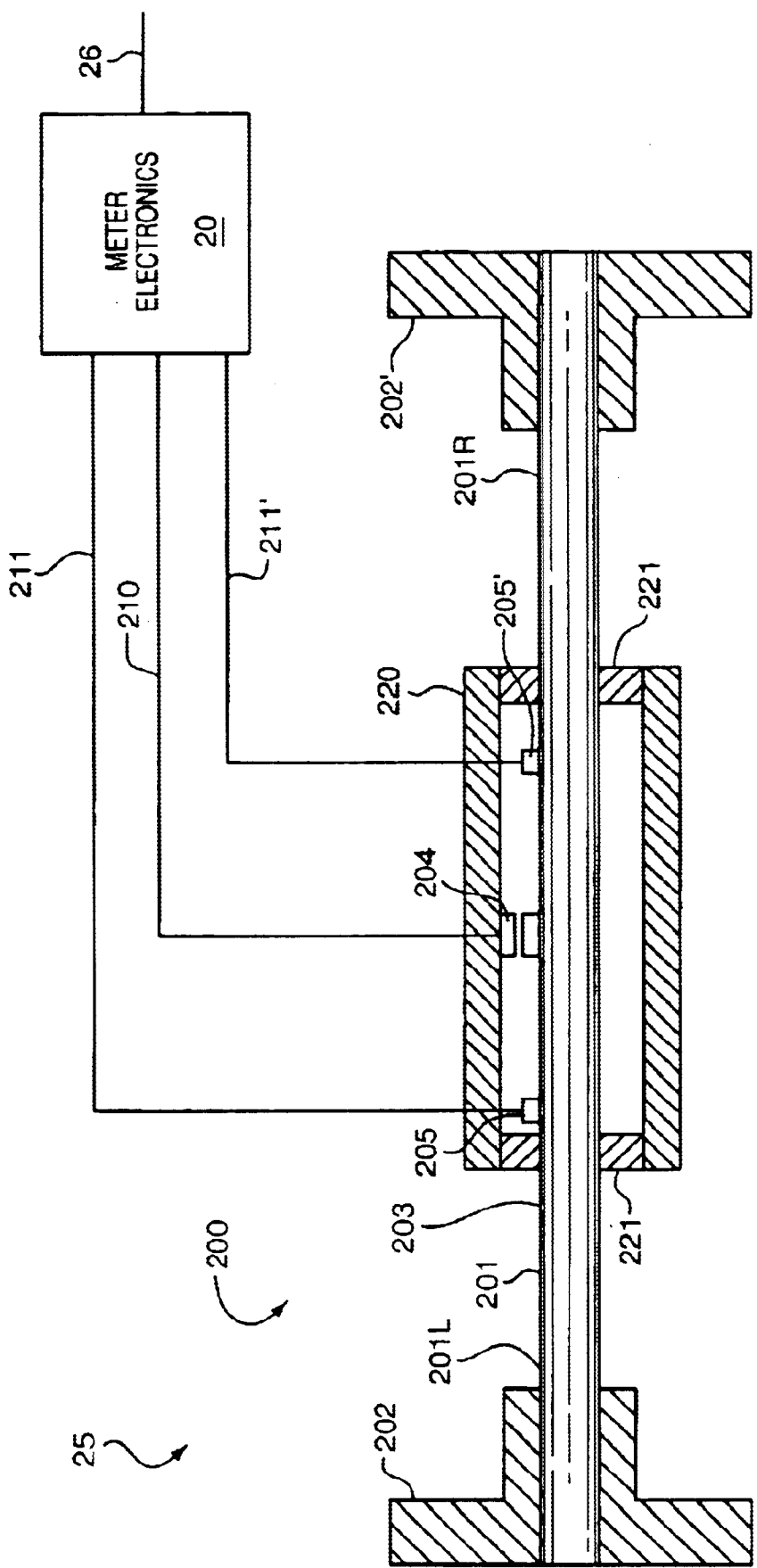
FIG. 2 illustrating a single straight flow tube Coriolis flowmeter incorporating a system for determining properties of the flow tube and of a fluid flowing through the flow tube in accordance with the invention.
Figure 3:
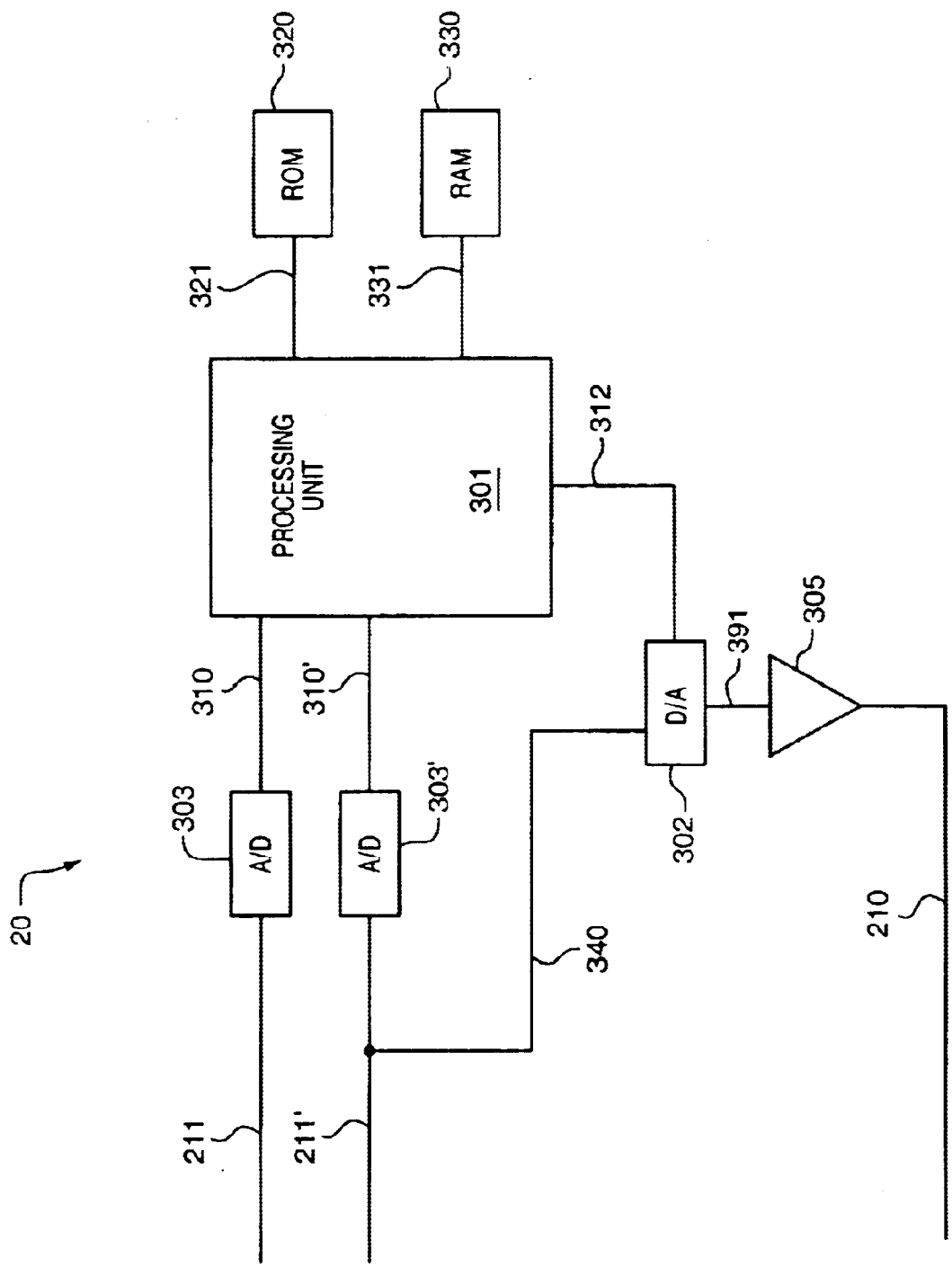
FIG. 3 illustrating meter electronics incorporating a system for determining properties of the flow tube and of a fluid flowing through the flow tube in accordance with the invention.

FIGS. 1–3 illustrate an environment in which to implement the invention. The invention is not limited to the embodiments in FIGS. 1–3, but is defined by the claims.
Dual Tube Coriolis Flowmeter—FIG. 1

FIG. 1 shows a dual tube Coriolis flowmeter 5 comprising a Coriolis sensor 10 and associated meter electronics 20. Meter electronics 20 is connected to Coriolis sensor 10 via leads 100 to provide density, mass flow rate, volume flow rate, totalized mass flow, and other information over path 26. Flowmeter 5 is described although it is apparent to those skilled in the art that the present invention could be practiced in conjunction with any apparatus having a vibrating flow tube to measure properties of fluid. A second example of such an apparatus is a vibrating tube densitometer which does not have the additional measurement capability provided by a Coriolis mass flowmeter.

Coriolis sensor 10 includes a pair of flanges 101 and 101', manifold 102, and flow tubes 103A and 103B. Driver 104, pickoff 105, and pickoff 105' are connected to flow tubes 103A and 103B. Brace bars 106 and 106' serve to define the axis W and W' about which each flow tube oscillates. Those skilled in the art will appreciate that additional pickoffs may be needed to implement the invention. The invention is not limited to the configuration in FIG. 1 as FIG. 1 merely shows an example environment to implement the invention.

Coriolis sensor 10 is inserted into a pipeline system (not shown) which carries a process fluid that is being measured. The fluid enters sensor 10 through flange 101. The fluid passes through manifold 102 where the fluid is directed to enter flow tubes 103A and 103B. The fluid flows through flow tubes 103A and 103B and back into manifold 102 from where it exits sensor 10 through flange 101'.

Flow tubes 103A and 103B are selected and appropriately mounted to the manifold 102 so as to have substantially the same mass distribution, moments of inertia, and elastic modules about bending axes W—W and W'—W', respectively. The flow tubes 103A–103B extend outwardly from the manifold 102 in an essentially parallel fashion.

Flow tubes 103A–103B are driven by driver 104 in opposite directions about their respective bending axes W and W' at what is termed the first out of phase bending mode. Driver 104 may comprise any one of many well known arrangements, such as a magnet mounted to flow tube 103A and an opposing coil mounted to flow tube 103B and through which an alternating current is passed for vibrating both flow tubes 103A–103B. Meter electronics 20 supplies a drive signal to driver 104 via lead 110.

Meter electronics 20 receives the left and right velocity signals appearing on leads 111 and 111' from pickoffs 105 and 105', respectively. Meter electronics 20 produces the drive signal appearing on lead 110 and causing driver 104 to vibrate tubes 103A and 103B. Meter electronics 20 processes the left and right velocity signals to compute the mass flow rate and the density of the fluid passing through sensor 10. Meter electronics 20 transfers this information to auxiliary electronics (not shown) over path 26.

It is known to those skilled in the art that flowmeter 5 is quite similar in structure to a vibrating tube densitometer. Vibrating tube densitometers also utilize a vibrating tube through which fluid flows or, in the case of a sample-type densitometer, within which fluid is held. Vibrating tube densitometers also employ a drive system for exciting the flow tube to vibrate. Vibrating tube densitometers typically utilize only single feedback signal since a density measurement requires only the measurement of frequency and a phase measurement is not necessary. The descriptions of the present invention herein apply equally to vibrating tube densitometers.
A Straight Tube Coriolis Flowmeter—FIG. 2

FIG. 2 discloses a straight tube Coriolis flowmeter 25. Straight tube Coriolis flowmeter 25 is comprised of Coriolis sensor 200 and associated meter electronics 20. Coriolis sensor 200 is comprised of a single flow tube 201. Flow tube 201 includes a left end portion designated 201L, and a right end portion designated 201R. Flow tube 201 and its ends portions extend the entire length of the flowmeter 25 from the input end of flow tube 201 to the output end of flow tube 201. A balance bar 220 is connected at its ends to flow tube 201 by a brace bar 221.

Left end portion 201L of flow tube 201 is affixed to an inlet flange 202. Right end portion 201R is affixed to an outlet flange 202'. Inlet flange 202 and outlet flange 202' are configured to connect Coriolis sensor 200 to a pipeline (not shown).

In a well known conventional manner, a driver 204, a left pick off 205 and a right pick off 205' are coupled to flow tube 201 and balance bar 220. Driver 204 receives signals over path 210 from meter electronics 20 to cause driver 204 to vibrate flow tube 201 and balance bar 220 in phase opposition at the resonant frequency of the fluid-filled flow tube 201. The oscillation of vibrating flow tube 201 together with the fluid flow therein induces Coriolis deflections in the flow tube 201 in a well known manner. The pickoffs 205 and 205' detect Coriolis deflections and transmit signals that represent the Coriolis deflections over conductors 211 and 211' to meter electronics 20. Meter electronics 20 transfers information, such as the mass flow rate and density of the fluid, to auxiliary electronics (not shown) over path 26.

Those skilled in the art will appreciate that a dual-straight tube could also be used similar to FIG. 2.

Meter Electronics—FIG. 3

FIG. 3 illustrates components of meter electronics 20. Meter electronics 20 is shown as connected to sensor 200 in FIG. 2. Paths 211–211' transmit the left and right velocity signals from sensor 200 to meter electronics 20. The velocity signals are received by analog to digital (A/D) convertor 303 in meter electronics 20. A/D convertor 303 converts the left and right velocity signals to digital signals usable by processing unit 301 and transmits the digital signals over path 310–310'. Although shown as separate components, A/D convertor 303 may be a signal convertor, such a CS4218 Stereo 16-bit codec chip manufactured of Crystal Semi Inc. The digital signals are carried by paths 310–310' to processing unit 301. One skilled in the art will recognize that any number of pickoffs and other sensors, such as an RTD sensor for determining the temperature of the flow tube, may be connected to processing unit 301.

Driver signals are transmitted over path 312 which applies the signals to digital to analog (D/A) convertor 302. D/A convertor 302 also receives voltage from one of pickoffs 205–205' over path 340. The drive signals include instructions for modifying the voltage received over path 340 to generate an analog drive signal. D/A convertor 302 is a common D/A convertor such as the AD7943 chip produced by Analog Devices. The analog signals from D/A convertor 302 are transmitted to amplifier 305 via path 391. Amplifier 305 generates a drive signal of the proper amplitude and transmits the drive signal to driver 204 via path 210. Amplifier 305 may be a current amplifier or a voltage amplifier. Path 26 carries signals to auxiliary electronics (not shown) which allow meter electronics 20 to receive data from and convey data to an operator.

Processing unit 301 is a micro-processor, processor, or group of processors that reads instructions from memory and executes the instructions to perform the various functions of the flowmeter. In a preferred embodiment, processor 301 is a ADSP-2185L microprocessor manufactured by Analog Devices. The functions performed include, but are not limited to, computing mass flow rate of a fluid, computing volume flow rate of a fluid, and computing density of a fluid from a Read Only Memory (ROM) 320 via path 321. The data, as well as instructions for performing the various functions, are stored in a Random Access Memory (RAM) 330. Processor 301 performs read and write operations in RAM memory 330 via path 331.

General Overview

This invention relates to determining properties of a flow tube and of a fluid flowing through the flow tube. After the general overview, a description of the processes used to determine properties of a flow tube and of a fluid flowing through the flow tube are described.

One method of looking at a flow tube through which fluid is flowing is as a Euler/Bernoulli beam under tension. Those skilled in the art will appreciate that other models can be used, such as a Timoshenko beam model. A homogeneous differential equation for a beam, such as a flow tube of a Coriolis flowmeter, is:

$$EI_{tube} \frac{\delta^4 y(x,t)}{\delta x^4} + \rho A \frac{\delta^4 y(x,t)}{\delta t^2} - S \frac{\delta^2 y(x,t)}{\delta x^2} = 0 \quad (1)$$

where:

$EI_{tube}$=flexural rigidity of the flow tube;

S=tension of the flow tube; and $\rho A$=combined mass/unit length of the flow tube and fluid.

The third term on the left side of equation (1) is a tension/compression term of the flow tube. By convention, S is positive for tension and negative for compression. Separation of variables may be applied to y(x,t) to get a solution in the following form:

$$y(x,t) = \sum_{r=1}^{\infty} \phi_r(x) \eta_r(t) = \sum_{r=1}^{\infty} \phi_r(x) e^{j\omega_r t} \quad (2)$$

where:

$\phi_r$=a function describing the mode shape in terms of spatial coordinates; and $\eta_r(t)$=the modal response as a function of time.

For purposes of this discussion, the summation of modal analysis is dropped. Therefore, the differential equation for a "per mode" basis is:

$$\Phi_r(X) = e^{\lambda_r X} \eta_r(t) = e^{j\omega_r t} \quad (3)$$

where:

$\Phi_r(X)$=the eigenvector of the rth mode;

$\lambda_r$=eigenvalue of the rth mode; and $\omega_r$=damped natural frequency of the $r^{th}$ mode.

The substitution of equations (2) and (3) into equation (1) yields:

$$\left(\lambda_r^4 - \frac{S}{EI_{tube}} \lambda_r^2 - \frac{\rho A}{EI_{tube}} \omega_r^2\right) e^{\lambda_r X} e^{j\omega_r t} = 0 \quad (4)$$

It is possible to solve for the roots of $\lambda_r$ and obtain an equation for any mode shape. Solving for $\lambda_r$ yields:

$$\lambda_r = \pm \left[\frac{-b_r \pm \sqrt{b_r^2 - 4c_r}}{2}\right] \quad (5)$$

where:

$$b_r = -\frac{S}{EI_{tube}}; \text{ and}$$

$$c_r = \frac{\rho A}{EI_{tube}} \omega_r^2.$$

From the above equations, it is known that $\lambda_r$ will have two real and two imaginary roots in the following manner:

$$\lambda 1_r = \pm \left[ \frac{-b + \sqrt{b^2 - 4c}}{2} \right]^{1/2} ; \text{ and} \qquad (6), (7)$$

$$\lambda 2_r = \pm \left[ \frac{b + \sqrt{b^2 - 4c}}{2} \right]^{1/2}$$

Since S/EI, ρA/EI, and $\omega_r$ are used to determine the eigenvalues, these terms can be referred to as eigenvalue parameters. S/EI and ρA/EI can also be referred to as flow tube and fluid parameters.

The function for determining the mode shape, or eigenvector, of any mode is given in the following equation:

$$\Phi_r(x) = C1_r e^{\lambda 1_r x} + C2_r e^{-\lambda 1_r x} + C3_r e^{j\lambda 2_r x} + C4_r e^{-j\lambda 2_r x} \qquad (8)$$

where:

$C1_r$, $C2_r$, $C3_r$, and $C4_r$ represent boundary condition coefficients for the $r^{th}$ mode.

Alternatively, equation (8) may be expressed in dot product form in the following manner:

$$\Phi_r(x) = \begin{bmatrix} e^{\lambda 1_r x} & e^{-\lambda 1_r x} & e^{j\lambda 2_r x} & e^{j\lambda 2_r x} \end{bmatrix} \begin{Bmatrix} C1 \\ C2 \\ C3 \\ C4 \end{Bmatrix}_r = \qquad (9)$$

$$\exp([\lambda 1_r x \quad -\lambda 1_r x \quad j\lambda 2_r x \quad -j\lambda 2_r x]) \begin{Bmatrix} C1 \\ C2 \\ C3 \\ C4 \end{Bmatrix}_r$$

This formula will be used later to determine the boundary conditions. Typically, the solution for modal frequencies requires that four boundary conditions at two ends of the flow tube are known. These boundary conditions are solved for from the equation for modal frequencies, i.e. equations (8) and (9).

In order to determine the boundary conditions, the frequencies of the modes are measured at "p" discrete locations given that nominal values are known for the physical properties and fluid properties of the flow tube. To solve for the boundary conditions, four or more pickoffs are used to measure the mode shapes and are referred to as boundary condition pickoffs. One or more pickoffs, called the reference pickoffs, are then used to measure a reference value. The reference value is compared to the estimated mode shape to determine error in the mode shapes. These reference pickoffs may be located anywhere except coincident to the boundary condition pickoffs. Let {x} be the locations of the boundary condition pickoff locations along the flow tube. Therefore:

$$\{x\} = \begin{Bmatrix} x_1 \\ \vdots \\ \vdots \\ x_p \end{Bmatrix} \qquad (10)$$

where:

$p \geq 4$.

From the above description of {x}, equation (9) may be expanded into matrix form to yield:

$$\begin{Bmatrix} \Phi_r(x_1) \\ \vdots \\ \Phi_r(x_p) \end{Bmatrix} = \begin{bmatrix} e^{\lambda 1_r x_1} & e^{-\lambda 1_r x_1} & e^{j\lambda 2_r x_1} & e^{-j\lambda 2_r x_1} \\ \vdots & \vdots & \vdots & \vdots \\ e^{\lambda 1_r x_p} & e^{-\lambda 1_r x_p} & e^{j\lambda 2_r x_p} & e^{-j\lambda 2_r x_p} \end{bmatrix} \begin{Bmatrix} C1_r \\ C2_r \\ C3_r \\ C4_r \end{Bmatrix} = [B]_r [C]_r \qquad (11)$$

If the eigenvalues $\lambda 1_r$ and $\lambda 2_r$ are known, then the boundary condition may be quantified by taking a pseudo inverse of $[B]_r$, using a least squares fit technique, such that:

$$\{C\}_r = [B_r]^+ \{\Phi_r(x)\} \qquad (12)$$

According to the Euler/Bernoulli model, an eigenvalue of each mode is made up of the following three variables S/EI, ρA/EI, $\omega_r$. S/EI is the ratio of tension to flexural rigidity, ρA/EI is the ratio of mass per unit length to flexural rigidity, and $\omega_r$, is the modal frequency. Modal frequencies may be measured very accurately using boundary condition pickoff signal analysis. Furthermore, S/EI and ρA/EI are nominally known. In other words, estimated values of these two variables may be determined from published nominal values found in textbooks or other published standards. An optimization technique may then be used to find optimal values for these variables within an acceptable error range. Once S/EI and ρA/EI are solved for, properties of a flow tube and of a fluid flowing through the flow tube maybe determined as set forth below.

Figure 4:
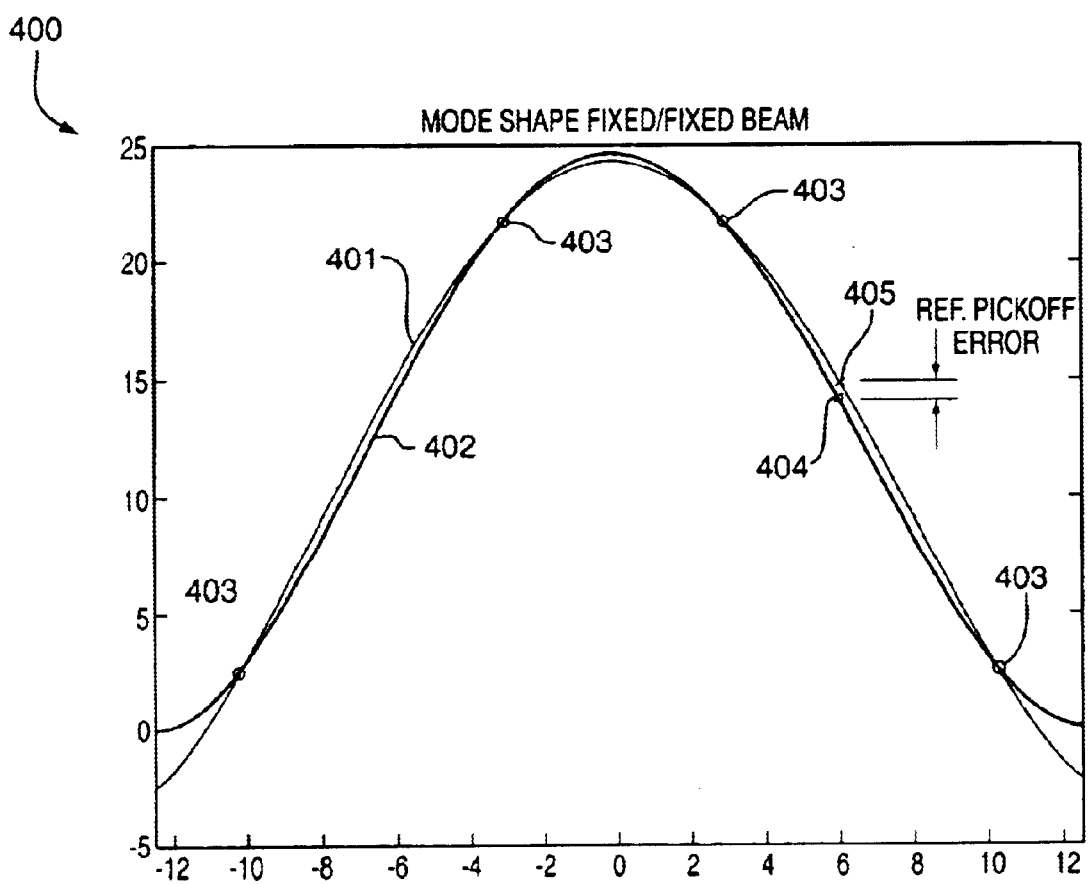
FIG. 4 illustrating a measured mode shape of a flow tube compared to an estimated mode shape in accordance with the invention.

The relationship between the estimated values of S/EI and ρA/EI are shown in graph 400 of FIG. 4. Line 402 is a measured mode shape of an $r^{th}$ mode of vibration. The measured mode shape is generated from pickoff signals. In graph 400, the mode is the first bending mode of the flow tube. Line 401 is an estimated mode shape based upon the estimated values of flow tube and fluid parameters S/EI and ρA/EI. Points 403 are pickoff values from boundary condition pickoffs that are used to determine boundary locations, $\{C\}_r$, using equation (12). Point 404 is an actual measured reference pickoff value. Point 405 is the estimated reference pickoff value based upon the estimated values for S/EI and ρA/EI.

Figure 5:
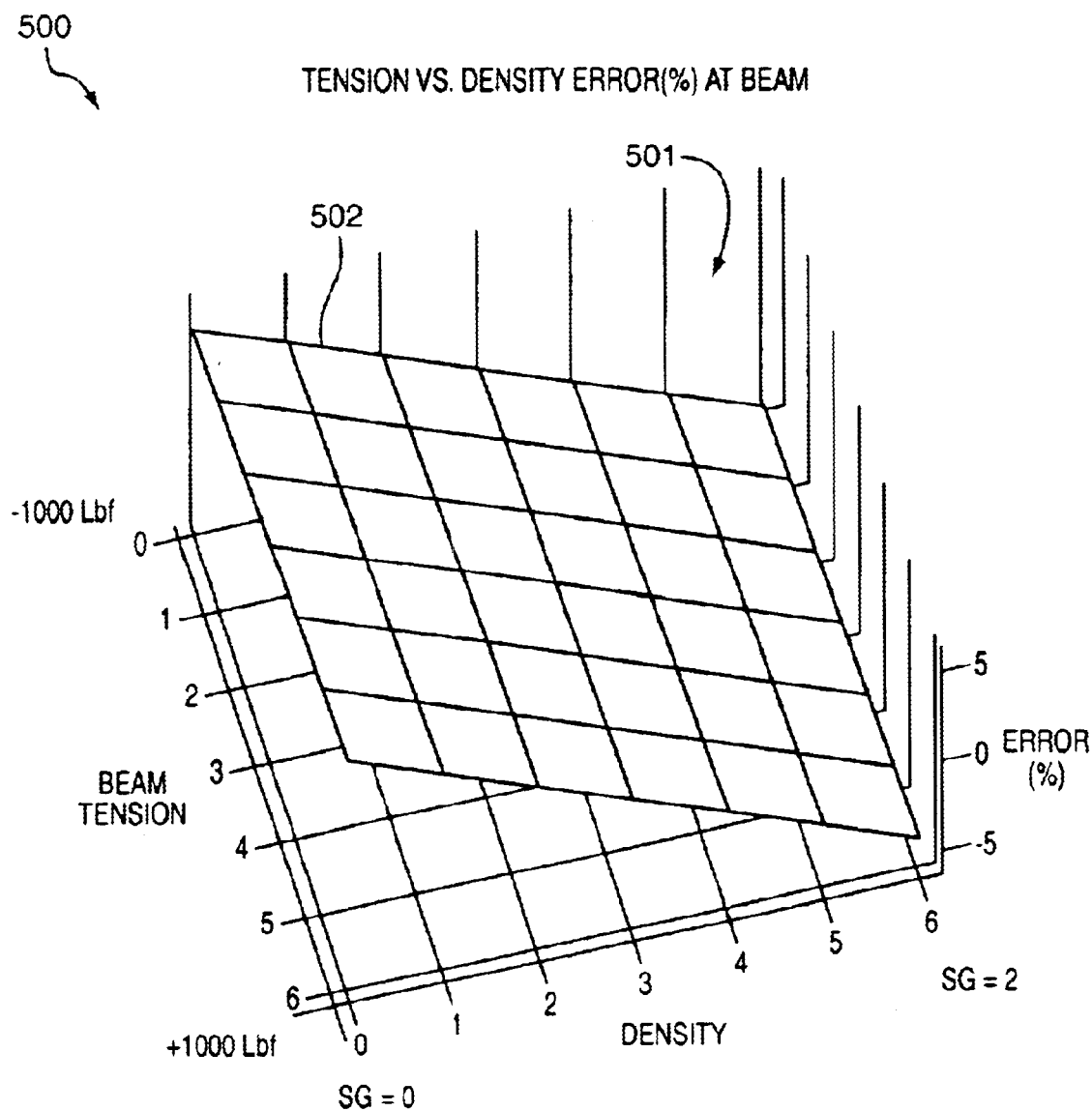
FIG. 5 illustrating a error surface of a first bending mode from modal analysis in accordance with the invention.

FIG. 5 illustrates a three dimensional graph 500 that shows an error plane 502 of error surfaces for a range of estimated values for the first bending mode of a flow tube. Graph 500 is for the first bending mode of the flow tube. Plane 501 is a zero error plane. The intersection of the error plane 502 and the zero error plane 501 is an error curve. Any value for S/EI and ρA/EI on the error curve could be a valid estimate because the reference pickoff error for these solutions is approximately zero. To further narrow the potential estimated values and to find the optimum value of S/EI and ρA/EI, information for another mode of vibration of the flow tube can be used. Even though the valid estimated values have been narrowed to the values on the error curve, there is still an infinite number of values on the error curve.

Figure 6:
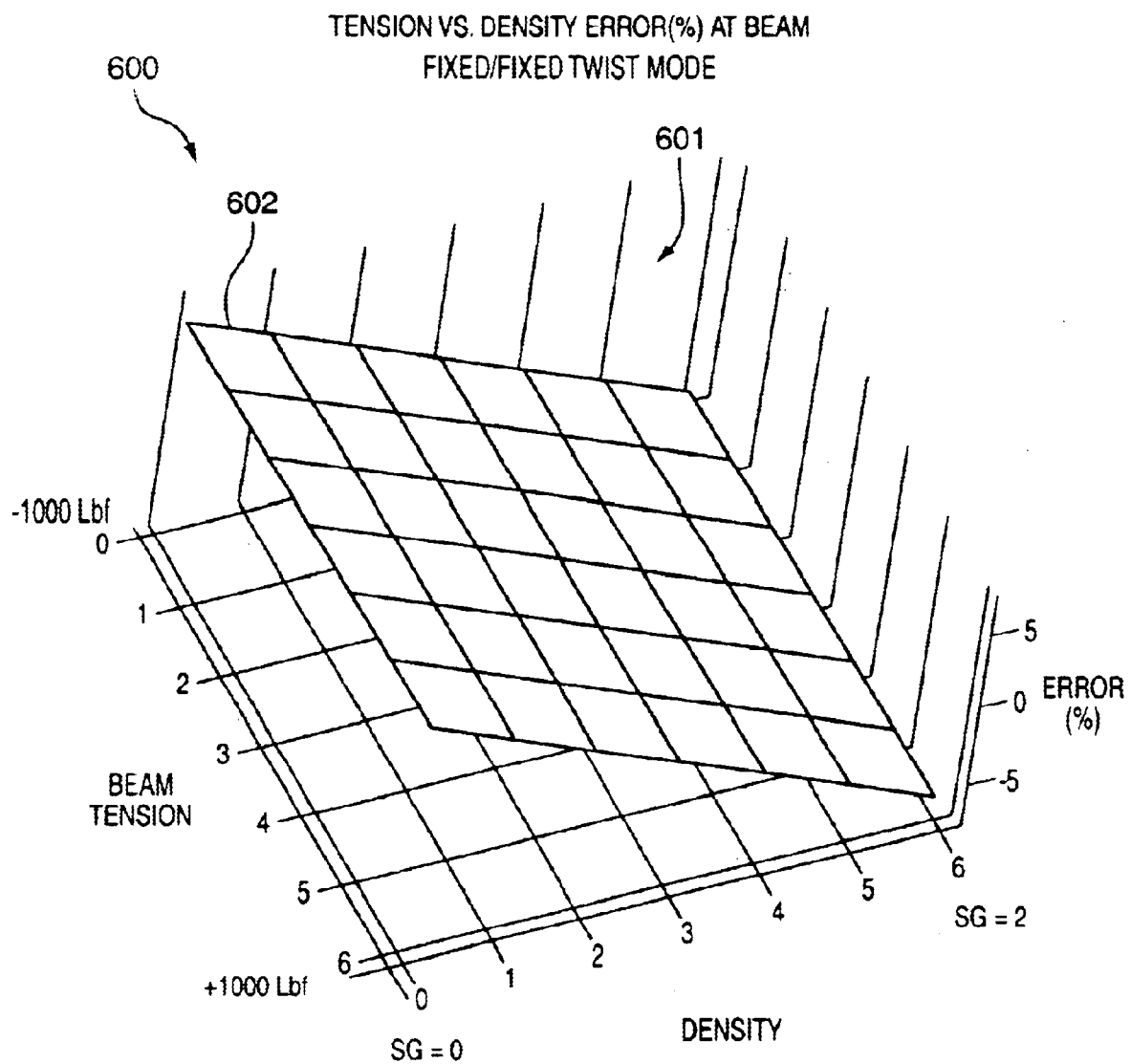
FIG. 6 illustrating an error surface of a twist mode from modal analysis in accordance with the invention.

FIG. 6 illustrates a graph 600 of an error plane 602 for the second bending mode of the flow tube, referred to as the "twist" mode. Plane 601 is a zero error plane. By comparing graphs 500 and 600, one can see that the error curve of the intersection with the zero error plane is different. Therefore, the estimated values of S/EI and ρA/EI of the two error curves minimize the error in both mode shapes. As the error curve minimizes and converges to zero, the estimated values for the flow tube and fluid parameters become optimized.

Mathematically, the intersection of two error planes and the zero error plane is a point. Therefore, correct values for S/EI and ρA/EI can be determined from a calculation of the intersection of the three planes. After each estimate for S/EI and ρA/EI are made, there will probably still be some error. However, the error has been reduced. A further improvement in the error can be found by again estimating values for S/EI and ρA/EI in the area of the new estimate and getting a better estimate than the last. Looping through in this way will result in a better estimate until the error is at an acceptable level. Once the optimum values for S/EI and ρA/EI are determined, the eigenvalues for the modes of vibration are determined and the boundary conditions are determined. Once these values are determined, the properties of the flow tube and of the fluid flowing through the flow tube may be determined.

Method for Determining Properties of a Flow Tube and Fluid—FIGS. 7–13

Figure 7:
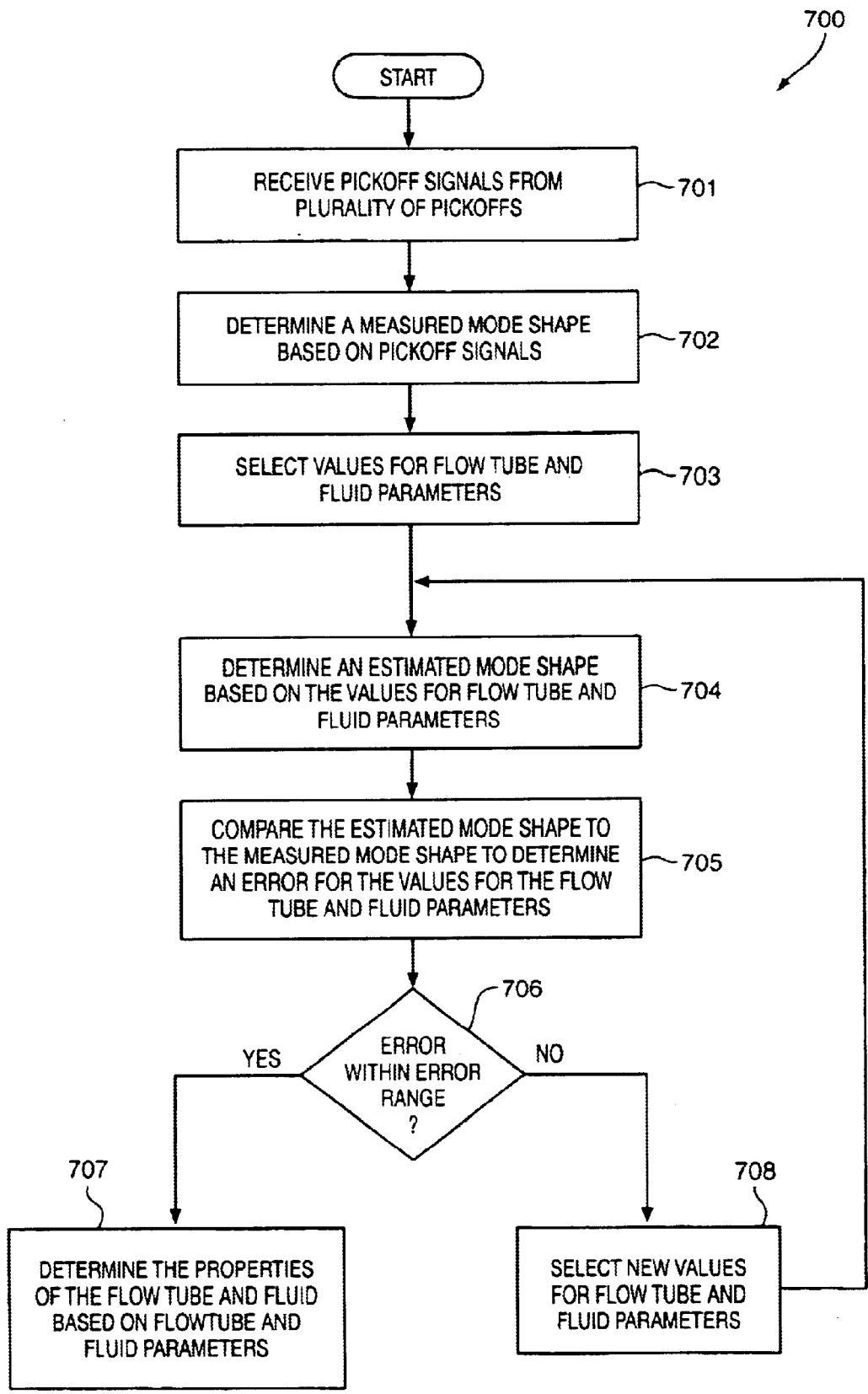
FIG. 7 illustrating a flow diagram of a process for determining properties of the flow tube and of a fluid flowing through the flow tube in accordance with the invention.

FIG. 7 illustrates a process 700 for determining properties of a flow tube and of a fluid flowing through the flow tube based on the above theory. Process 700 could be performed by meter electronics 20 for example. In this example, the flow tube refers to flow tube 201 in FIG. 2. In step 701, process 700 receives pickoff signals from the plurality of pickoffs 205, 205'. In some examples, process 700 also receives a known excitation of a driver connected to the flow tube(s). In step 702, process 700 determines a measured mode shape of flow tube 201 based on the pickoff signals. In step 703, process 700 selects values for flow tube and fluid parameters. The flow tube and fluid parameters are any parameters that represent physical properties of a flow tube or a fluid flowing through the flow tube. For example, the flow tube and fluid parameters could be a ratio of tension to flexural rigidity of the flow tube, and/or a ratio of mass per unit length to flexural rigidity of the flow tube. In step 704, process 700 determines an estimated mode shape of flow tube 201 based on the values for the flow tube and fluid parameters. In step 705, process 700 compares the estimated mode shape to the measured mode shape to determine an error for the values for flow tube and fluid parameters. In step 706, process 700 determines if the error for the values for flow tube and fluid parameters is within an error range. One example of the error range is approximately +/−0.1%.

If the error for the values is within the error range, then process 700 determines the properties of the flow tube and of the fluid flowing through the flow tube based on at least one of the values for flow tube and fluid parameters in step 707.

In some examples, if the error for the values is not within the error range, then process 700 selects new values for the flow tube and fluid parameters in step 708. Process 700 then repeats steps 704 and 706 using the new values.

In some examples, meter electronics 20 determines a density of the fluid flowing through flow tube 201 based on the flow tube and fluid parameters. To determine the density, meter electronics 20 determines density calibration factors. To determine the density calibration factors, meter electronics 20 receives the pickoff signals from pickoffs 205, 205' indicating motion of flow tube 201 as a first fluid flows through flow tube 201. The first fluid has a known density. Meter electronics 20 generates first factors based on the pickoff signals. Meter electronics 20 then receives pickoff signals from pickoffs 205, 205' indicating motion of flow tube 201 as a second fluid flows through flow tube 201. The second fluid also has a known density. Meter electronics 20 generates second factors based on the pickoff signals. Meter electronics 20 determines the density calibration factors based on the first and second factors. Meter electronics 20 uses the density calibration factors to determine a density of a fluid flowing through flow tube 201.

In some examples, a first one of the density calibration factors comprises a ratio of area per unit length of the fluid to a flexural rigidity of the flow tube. And, a second one of the density calibration factors comprises a ratio of mass per unit length of the flow tube to the flexural rigidity of the flow tube. And, a first one of the values for the flow tube and fluid parameters comprises a ratio of mass per unit length of the fluid and flow tube to the flexural rigidity of the flow tube. In such a case, meter electronics 20 determines the density of the fluid by subtracting the second one of the density calibration factors from the first one of the values for the flow tube and fluid parameters to yield a first result. Meter electronics 20 then multiplies the first result by an inverse of the first one of the density calibration factors to determine the density of the fluid flowing through flow tube 201. Mathematical equations that illustrate the above process follow.

Figure 8:
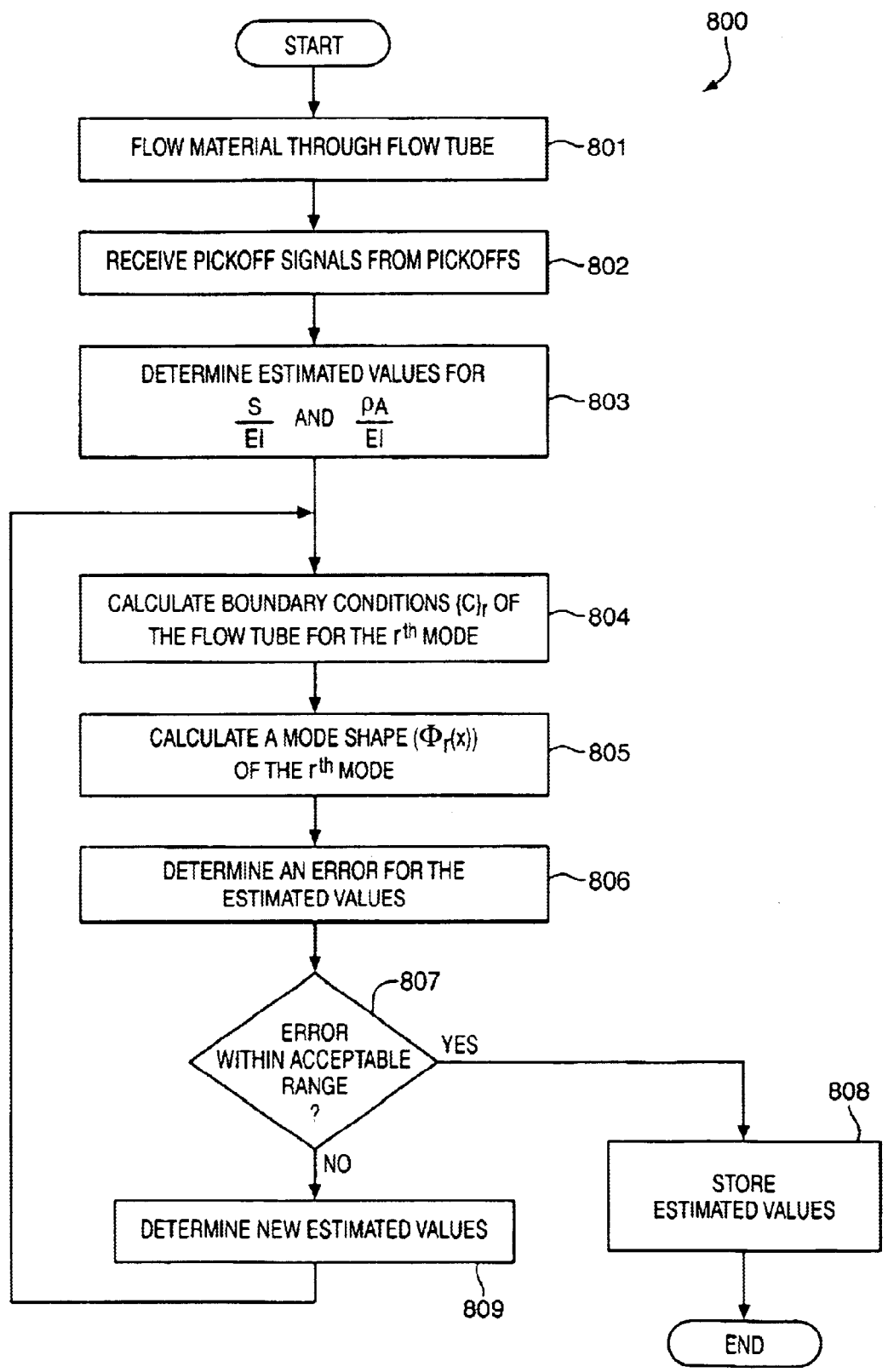
FIG. 8 illustrating a flow diagram of a process for determining boundary conditions and estimated values of flow tube and fluid parameters in accordance with the invention.

FIG. 8 illustrates a process 800 for determining boundary conditions and density of a fluid by determining estimated values having an acceptable error. Process 800 begins with the fluid being flowed through the flow tube 201 in step 801. In step 802, process 800 receives pickoff signals from pickoffs 205, 205'. In step 803, process 800 determines estimated values for the S, I, G, $A_{tube}$, $A_{fluid}$, E, I, $\rho_{tube}$, $\rho_{fluid}$, where:

S=the tension acting on the flow tube;

I=area moment of inertia of the flow tube;

$A_{fluid}$=area of the fluid which is the inside diameter of the flow tube;

E=the modulus of elasticity of the flow tube;

$\rho_{tube}$=density of the flow tube; and $\rho_{fluid}$=density of the fluid flowing through the flow tube.

Figure 9:
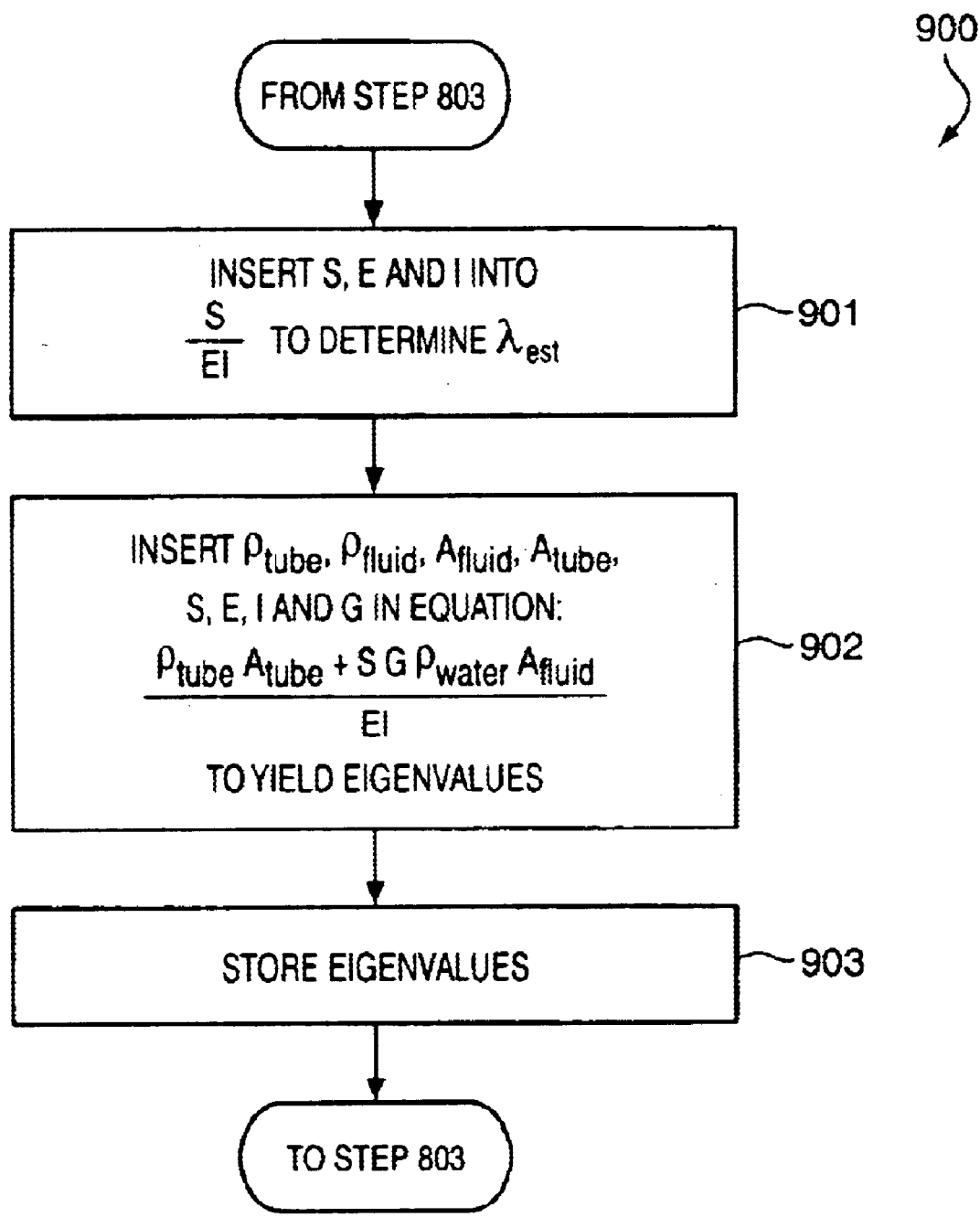
FIG. 9 illustrating a flow diagram of a process for determining eigenvalues for a mode of vibration of a flow tube in accordance with the invention.
Figure 10:
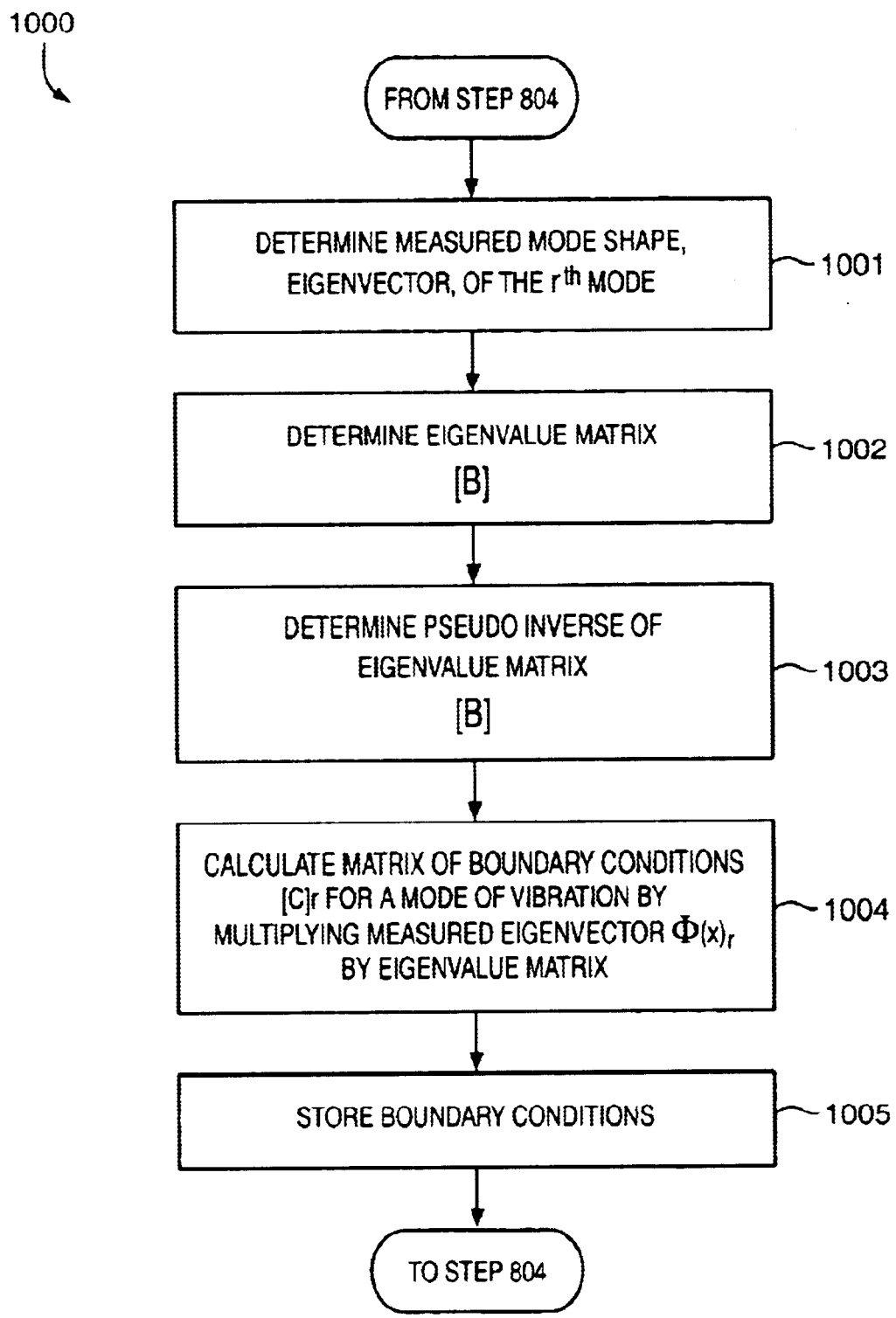
FIG. 10 illustrating a flow diagram of a process for determining boundary condition functions in accordance with the invention.

FIG. 9 illustrates a process for determining the estimated values in step 803. Process 900 begins in step 901 with by inserting S, E, and I into the equation S/EI. In most cases, three values of S are given resulting in three different estimated values. In step 902, process 900 inserts S, G, $A_{fluid}$, $A_{tube}$, E, I, $\rho_{tube}$, and $\rho_{water}$ into the equation:

$$\frac{\rho_{tube}A_{tube} + SG\rho_{water}A_{fluid}}{EI} \quad (13)$$

This equation generates eigenvalues for the estimated values. In step 903, process 900 stores the eigenvalues.

Referring back to FIG. 8, process 800 continues in step 804 by using the modal parameters measured by the signals received from the pickoffs to determine the boundary conditions. Boundary conditions are determined in the following manner shown in FIG. 10. Process 1000 begins in step 1001, by determining the eigenvectors for each mode of vibration from the signals measured by the pickoffs 205, 205'. In step 1002, process 1000 determines a matrix [B] of eigenvalues generated from the estimated values. The eigenvalue matrix [B] is shown in equation (11). The pseudo inverse of the eigenvalue matrix [B] is then determined in step 1003. Then, in accordance with equation (12), process 1000 calculates a matrix of boundary conditions $[C]_r$ by multiplying the eigenvectors of the $r^{th}$ mode of vibration with the pseudo inverse of the eigenvalue matrix $[B]^+$ in step 1004. In step 1005, process 1000 stores the boundary conditions and process 1000 ends.

Referring back to FIG. 8, process 800 continues in step 805 by calculating a mode shape for the $r^{th}$ mode of vibration. The following equation is used to determine the mode shape, or eigenvector, for the $r^{th}$ mode using the determined eigenvalues.

$$\Phi_r(x_{ref})_{est} = \exp([\lambda 1_{est}x_{ref} - \lambda 1_{est}x_{ref}j\lambda 2_{est}x_{ref} - j\lambda 2_{est}x_{ref}])\{C\}_r \quad (14)$$

In step 806, process 800 compares the estimated mode shape to the measured mode shape from step 1001 to determined whether the error is acceptable. If the error is acceptable in step 807, then process 800 stores the estimated values in step 808. If the error is not acceptable, then process 800 determines new estimate values in step 809 and returns to step 804.

Figure 11:
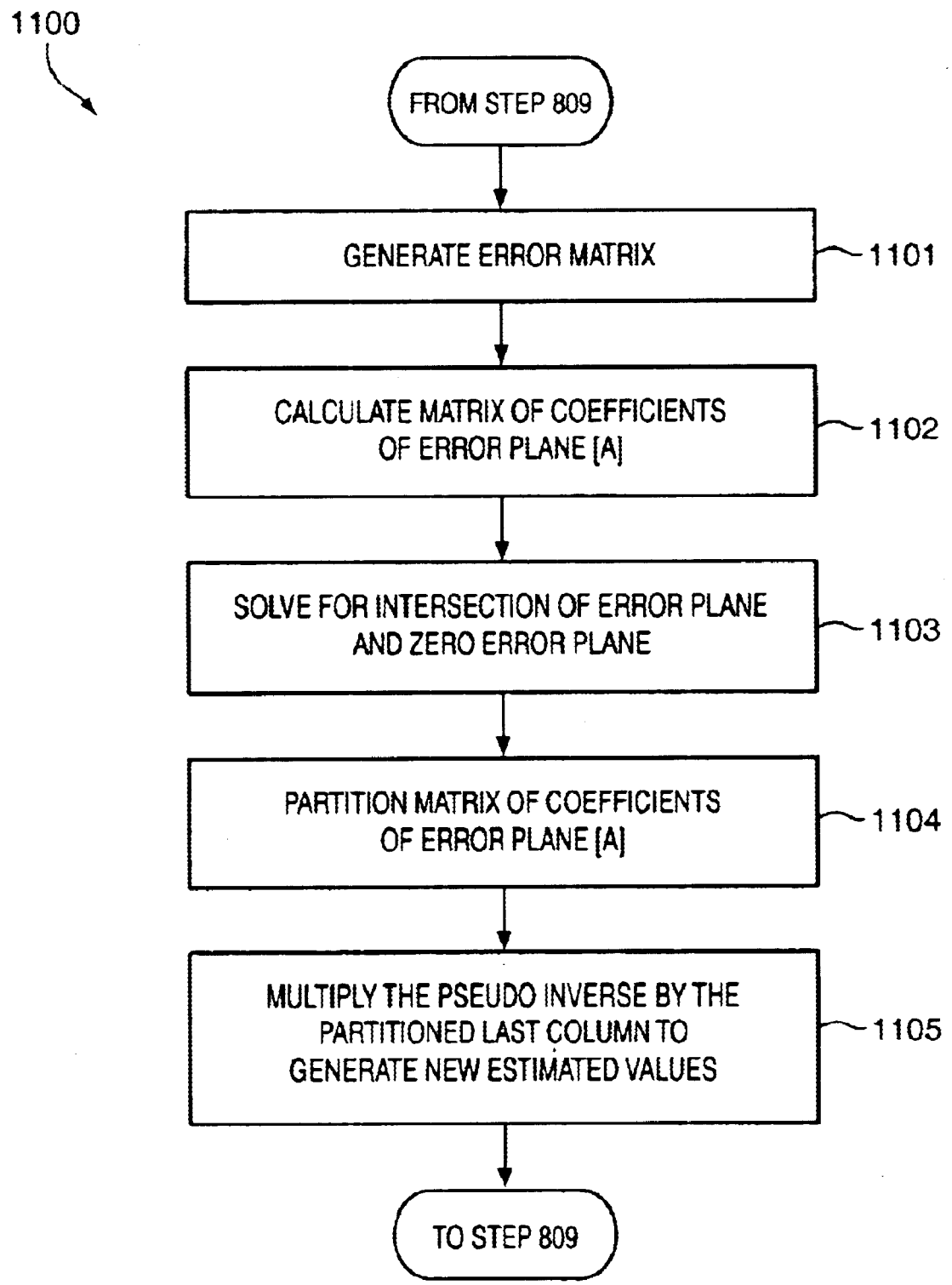
FIG. 11 illustrating a flow diagram of a process for generating new estimated values of flow tube and fluid parameters in accordance with the invention.

FIG. 11 shows a process 1100 for determining new estimated values in an example of the invention. Process 1100 begins in step 1101 by determining an error matrix. The error matrix is the matrix of error values expressed from the following equation:

$$\epsilon_r = \Phi_r(x_{ref})_{measured} - \Phi_r(x_{ref})_{est} \tag{15}$$

The error matrix therefore takes the form of:

$$\begin{bmatrix} \epsilon 1_1 & \cdots & \epsilon 1_r \\ \epsilon 2_1 & \cdots & \epsilon 2_r \\ \epsilon 3_1 & \cdots & \epsilon 3_r \end{bmatrix} = \tag{16}$$

$$\begin{bmatrix} \frac{\rho_{tube}A_{tube} + SG_1\rho_{fluid}A_{fluid}}{EI} & \frac{S_1}{EI} & 1 \\ \frac{\rho_{tube}A_{tube} + SG_2\rho_{fluid}A_{fluid}}{EI} & \frac{S_2}{EI} & 1 \\ \frac{\rho_{tube}A_{tube} + SG_3\rho_{fluid}A_{fluid}}{EI} & \frac{S_3}{EI} & 1 \end{bmatrix}_{g,3} \begin{bmatrix} a_1 & \cdots & a_r \\ b_1 & \cdots & b_r \\ c_1 & \cdots & c_r \end{bmatrix}_{3,r}$$

Alternatively, equation (16) may be expressed as:

$$[\epsilon] = [G][A] \tag{17}$$

where [A] is the matrix of coefficients of the error plane. The indices "g" represents the number of estimated values and "r" represents the number of modes of vibration.

In step 1102, process 1100 calculates the matrix of coefficients of the error plane [A]. [A] is calculated by taking the pseudo inverse of the guess matrix, [G], and multiplying by the error matrix [ε].

To determine the new estimated values, process 1100 solves for the intersection of the approximate error plane and the zero error plane, in step 1103, represented by the following equation:

$$\{0\} = [A]^T \begin{Bmatrix} \frac{\rho A}{EI} \\ \frac{S}{EI} \\ 1 \end{Bmatrix}_{est} \tag{18}$$

The last term of equation (18) is a better guess for the estimated values. This is done by partitioning $[A]^T$ to isolate the last column in step 1104 such that:

$$\{0\} = \begin{bmatrix} A_1 & B_1 & | D_1 \\ \vdots & \vdots & \vdots \\ A_r & B_r & | D_r \end{bmatrix} \begin{Bmatrix} \frac{\rho A}{EI} \\ \frac{S}{EI} \\ 1 \end{Bmatrix}_{est} = \begin{bmatrix} A_1 & B_1 \\ \vdots & \vdots \\ A_r & B_r \end{bmatrix} \begin{Bmatrix} \frac{\rho A}{EI} \\ \frac{S}{EI} \end{Bmatrix}_{est} + \begin{Bmatrix} D_1 \\ \vdots \\ D_r \end{Bmatrix} 1 \tag{19}$$

The new estimated values are then calculated in step 1105 and process 1100 ends. Process 1100 calculates the new estimated values by multiplying the pseudo inverse of the remaining terms by the partitioned last column, which is shown as:

$$\begin{Bmatrix} \frac{\rho A}{EI} \\ \frac{S}{EI} \end{Bmatrix}_{est} = \begin{bmatrix} A_1 & B_1 \\ \vdots & \vdots \\ A_r & B_r \end{bmatrix}^+ \begin{Bmatrix} D_1 \\ \vdots \\ D_r \end{Bmatrix} \tag{20}$$

The density of the fluid is calculated once acceptable estimated values are determined based upon the following premises. First, recall that in a Euler/Bernoulli beam:

$$\frac{\rho A}{EI_{tube}} = \frac{\rho_{tube}A_{tube} + \rho_{fluid}A_{fluid}}{EI_{tube}} \tag{21}$$

The mass per unit length of the flow tube is nominally known. The physical and fluid properties are also nominally known. Thus, if the flow tube is calibrated using two fluids of known density, such as air and water, then the density of another fluid may be determined since:

$$\frac{\rho A}{EI_{tube}} = [\rho_{fluid} \quad 1] \begin{Bmatrix} \frac{A_{tube}}{EI_{tube}} \\ \frac{\rho_{tube}A_{tube}}{EI_{tube}} \end{Bmatrix} \tag{22}$$

From above, it can be seen that calibration using two fluids of known density is done to measure $A_{fluid}/EI_{tube}$ and $\rho_{tube}A/EI_{tube}$, which are referred to as density calibration factors. Therefore, if $\rho A/EI_{tube}$ is determined for two fluids of known density, then density calibration factors can be determined because:

$$\begin{Bmatrix} \left(\frac{\rho A}{EI_{tube}}\right)_{fluid1} \\ \left(\frac{\rho A}{EI_{tube}}\right)_{fluid2} \end{Bmatrix} = \begin{bmatrix} \rho_{fluid1} & 1 \\ \rho_{fluid2} & 1 \end{bmatrix} \begin{Bmatrix} \frac{A_{fluid}}{EI_{tube}} \\ \frac{\rho_{tube}A_{tube}}{EI_{tube}} \end{Bmatrix} \tag{23}$$

Once the density calibration factors are determined, it can be assumed that physical properties of the conditions do not change. Thus, the density of the fluid flowing through the flow tube may be determined from the equation:

$$\rho_{fluid} = \left(\frac{\rho A}{EI_{tube}} - \frac{\rho_{tube}A_{tube}}{EI_{tube}}\right)\frac{EI_{tube}}{A_{fluid}} \tag{24}$$

Thus, once an acceptable value from $\rho_{tube}A/EI_{tube}$ is determined, the density of the fluid flowing through the flow tube can be found with the same certainty.

The above description is of a method to determine density through modal analysis. It is envisioned that one skilled in the art can and will design density measurement systems that infringe on this invention as set forth in the claims below either literally or though the Doctrine of Equivalents.

What is claimed is:

1. A method for determining properties of a flow tube and of a fluid flowing through said flow tube in response to receiving pickoff signals from a plurality of pickoffs associated with said flow tube, said pickoff signals indicating vibrations of said flow tube vibrated by a driver associated with said flow tube, said method comprising the steps of:
   a) receiving said pickoff signals from said plurality of pickoffs;
   b) determining a measured mode shape of said flow tube based on said pickoff signals;
   c) selecting values for flow tube and fluid parameters;

d) determining an estimated mode shape of said flow tube based on said flow tube and fluid parameters;

e) comparing said estimated mode shape to said measured mode shape to determine an error for said values for said flow tube and fluid parameters; and f) if said error for said values for said flow tube and fluid parameters is within an error range, then:
determining said properties of said flow tube and of said fluid flowing through said flow tube based on said values for said flow tube and fluid parameters.

2. The method of claim 1 further comprising:

(g) if said error for said values for said flow tube and fluid parameters is not within said error range, then:
selecting new values for said flow tube and fluid parameters; and
repeating steps (d)–(g).

3. The method of claim 1 wherein the step of determining said properties of said flow tube and of said fluid flowing through said flow tube comprises:
determining a density of said fluid flowing through said flow tube based on said values for said flow tube and fluid parameters.

4. The method of claim 3 further comprising the steps of:
flowing a first fluid of a known density through said flow tube and receiving said pickoff signals indicating motion of said flow tube as said first fluid flows through said flow tube to generate first factors;
flowing a second fluid of a known density through said flow tube and receiving said pickoff signals indicating motion of said flow tube as said second fluid flows through said flow tube to generate second factors; and
determining density calibration factors based on said first and second factors;
wherein said step of determining said density of said fluid flowing through said flow tube further comprises determining said density of said fluid flowing through said flow tube based on said values for said flow tube and fluid parameters and said density calibration factors.

5. The method of claim 4 wherein a first one of said density calibration factors comprises a ratio of area per unit length of said fluid to a flexural rigidity of said flow tube.

6. The method of claim 5 wherein a second one of said density calibration factors comprises a ratio of mass per unit length of said flow tube to said flexural rigidity of said flow tube.

7. The method of claim 6 wherein:
a first one of said values for said flow tube and fluid parameters comprises a ratio of mass per unit length of said fluid and said flow tube to said flexural rigidity of said flow tube; and
said step of determining said density of said fluid flowing through said flow tube comprises:
subtracting said second one of said density calibration factors from said first one of said values for said flow tube and fluid parameters to yield a first result; and
multiplying said first result by an inverse of said first one of said density calibration factors to determine said density of said fluid flowing through said flow tube.

8. The method of claim 1 wherein said plurality of pickoffs comprises at least four boundary condition pickoffs affixed to said flow tube and configured to generate said pickoff signals.

9. The method of claim 8 wherein said plurality of pickoffs further comprises at least one reference pickoff affixed to said flow tube and configured to generate a reference signal.

10. The method of claim 2 wherein said step of determining said new values for said flow tube and fluid parameters comprises comparing said flow tube and fluid parameters from at least two modes of vibration of said flow tube to determine said new values.

11. Meter electronics configured to determine properties of a flow tube and of a fluid flowing through said flow tube in response to receiving pickoff signals from a plurality of pickoffs associated with said flow tube, said pickoff signals indicating vibrations of said flow tube being vibrated by a driver associated with said flow tube, said meter electronics comprising:
a processing unit configured to read instructions from a storage media; and
said instructions configured to direct said processing unit to:
a) receive said pickoff signals from said plurality of pickoffs;
b) determine a measured mode shape of said flow tube based on said pickoff signals;
c) select values for flow tube and fluid parameters;
d) determine an estimated mode shape of said flow tube based on said flow tube and fluid parameters;
e) compare said estimated mode shape to said measured mode shape to determine an error for said values for said flow tube and fluid parameters; and
f) if said error for said values for said flow tube and fluid parameters is within an error range, then:
determine said properties of said flow tube and of said fluid flowing through said flow tube based on said values for said flow tube and fluid parameters.

12. The meter electronics of claim 11 wherein said instructions are further configured to direct said processing unit to:
(g) select new values for said flow tube and fluid parameters; and
repeat steps (d)–(g) if said error for said values for said flow tube and fluid parameters is not within said error range.

13. The meter electronics of claim 12 wherein said instructions are further configured to direct said processing unit to:
determine a density of said fluid flowing through said flow tube based on said values for said flow tube and fluid parameters.

14. The meter electronics of claim 13 wherein said instructions are further configured to direct said processing unit to:
generate first factors in response to receiving said pickoff signals indicating motion of said flow tube as a first fluid of a known density flows through said flow tube;
generate second factors in response to receiving said pickoff signals indicating motion of said flow tube as a second fluid of a known density flows through said flow tube;
determine density calibration factors based on said first and second factors; and
determine said density of said fluid flowing through said flow tube based further on said density calibration factors.

15. The meter electronics of claim 14 wherein a first one of said density calibration factors comprises a ratio of area per unit length of said fluid to a flexural rigidity of said flow tube.

16. The meter electronics of claim 15 wherein a second one of said density calibration factors comprises a ratio of mass per unit length of said flow tube to said flexural rigidity of said flow tube.

17. The meter electronics of claim 16 wherein:
- a first one of said values for said flow tube and fluid parameters comprises a ratio of mass per unit length of said fluid and said flow tube to said flexural rigidity of said flow tube; and
- wherein said instructions that are configured to direct said processing unit to determine said density of said fluid are further configured to direct said processing unit to:
  - subtract said second one of said density calibration factors from said first one of said values for said flow tube and fluid parameters to yield a first result; and
  - multiply said first result by an inverse of said first one of said density calibration factors to determine said density of said fluid flowing through said flow tube.

18. The meter electronics of claim 11 wherein said plurality of pickoffs comprises at least four boundary condition pickoffs affixed to said flow tube and configured to generate said pickoff signals.

19. The meter electronics of claim 18 wherein said plurality of pickoffs further comprises at least one reference pickoff affixed to said flow tube and configured to generate a reference signal.

20. The meter electronics of claim 12 wherein said instructions that are configured to direct said processing unit to determine said new values for said flow tube and fluid parameters are further configured to direct said processing unit to compare said flow tube and fluid parameters from at least two modes of vibration of said flow tube to determine said new values.

* * * * *